United States Patent [19]

Freytag et al.

[11] 4,021,231

[45] May 3, 1977

[54] METHOD FOR REDUCTION OF SUCROSE LOSS DURING STORAGE OR SUGAR BEETS DUE TO REDUCTION IN RESPIRATION AND INVERT SUGAR FORMATION

[75] Inventors: Arthur H. Freytag; Walter R. Akeson, both of Longmont, Colo.

[73] Assignee: The Great Western Sugar Company, Denver, Colo.

[22] Filed: May 14, 1974

[21] Appl. No.: 469,657

[52] U.S. Cl. .................................................. 71/127
[51] Int. Cl.² .......................................... A01N 9/00
[58] Field of Search ................. 71/68, 127, 70, 86

[56] References Cited

UNITED STATES PATENTS

| 2,285,932 | 6/1942 | Leavitt | 47/58 |
| 2,424,520 | 7/1947 | Tonkin | 47/58 |
| 3,184,891 | 5/1965 | Frontzen | 71/127 |
| 3,661,549 | 5/1972 | Freytag et al. | 71/127 X |

OTHER PUBLICATIONS

Wyse et al., Chem Abst., vol. 80 (1974) 105944r.
Tewari et al., Chem. Abst., vol. 81 (1974) 34449r.
Sagir et al., Chem Abst., vol. 76 (1972) 95618p.
Narayama, Chem. Abst., vol. 76 (1972) 95623m.

*Primary Examiner*—Lewis Gotts
*Assistant Examiner*—Catherine L. Mills
*Attorney, Agent, or Firm*—Bruce G. Klaas; Dennis K. Shelton

[57] ABSTRACT

Respiration of sucrose to carbon dioxide and water is reduced and the formation of invert sugar is inhibited in the storage of sugar beets which have had an effective amount of ethylene introduced into the ground near the roots of the growing plants.

2 Claims, No Drawings

METHOD FOR REDUCTION OF SUCROSE LOSS DURING STORAGE OR SUGAR BEETS DUE TO REDUCTION IN RESPIRATION AND INVERT SUGAR FORMATION

BACKGROUND OF THE INVENTION

Ethylene has received some attention as a potentially useful plant growth regulator. For example, ethylene and acetylene are described in U.S. Pat. No. 2,047,874 as being useful in either gaseous form or in an aqueous solution for causing pineapple and other plants to flower and mature sooner than they would otherwise. U.S. Pat. No. 2,084,461 is directed to the use of ethylene gas, or another unsaturated hydrocarbon gas such as butylene or propylene, for inducing uniformity of blooming and fruit production in fruiting plants, especially fruit trees. U.S. Pat. No. 3,661,549 is directed to the use of aqueous solutions of ethylene and compounds which yield ethylene for inducing growth of yield crops such as soybean and corn. Although some of the findings of the effects of treating plants with ethylene are interesting from a scientific point of view, they have not met with any substantial commercial success.

SUMMARY OF THE INVENTION

This invention is based upon the discovery that when sugar beets are treated with soil injected ethylene during growth, at 1.4 to 5 pounds ethylene per acre, the resulting sugar beets have about 20% less respiration during storage and have only about one third the usual amount of invert sugar as untreated sugar beets. This results in about a 20% increase in recoverable sucrose when the beets are processed.

DESCRIPTION OF PREFERRED EMBODIMENT

The depth beneath the ground surface and the distance from the sugar beet rows at which ethylene is introduced will depend upon several factors, as for example, the type of soil, moisture content of soil and the like. The depth at which ethylene is introduced for sugar beets is from about 6 to 8 inches at about 6 foot intervals in about the middle of the row when the sugar beets have reached the fifth leaf stage of growth.

The ethylene is introduced in an amount sufficient to reduce respiration and invert sugar formation. The ethylene is injected 6 to 8 inches deep in the soil at about 6 foot intervals near the middle of the rows when they have reached the fifth leaf stage of growth at a rate of about 1.4 to 2.8 pounds per acre with from one to three applications. The injections are made at the equivalent of late June or early July and the ethylene carries through its effects even after harvest. The treated sugar beets are found to have a much lower endogenous ethylene evolution from the tissues than untreated beets which in turn shows a much lower respiration during storage.

The respiration as set forth in Tables I and II was determined in respiration chambers in the following manner. Air which has been humidified and scrubbed clean of carbon dioxide is passed through respiration chambers each of which contained 20 pounds of sugar beets. The air flushed the carbon dioxide given off by respiration out of the chamber and the carbon dioxide is captured in a sodium hydroxide solution. The sodium hydroxide was back titrated with 0.5N hydrochloric acid to determine the amount of carbon dioxide evolved. Respiration measurements were carried out at 40° F. which is considered an ideal temperature for storage of beets.

TABLE I

Effect of Soil Injected Ethylene on Respiration
Sugar Loss - lb/Ton/Day

| Treatment in lbs/A | Numbers of Applications | Mean of Replications | Mean of All Ethylene Versus Control | Percent Difference |
|---|---|---|---|---|
| 0 | 0 | 0.389 | 0.389 | |
| 1.4 | 1 | 0.310 | | |
| 1.4 | 3 | 0.327 | 0.333 | −14.4 |
| 2.8 | 1 | 0.372 | | |
| 2.8 | 3 | 0.321 | | |

TABLE II

Effect of Soil Injected Ethylene on Respiration of Harvested Sugar Beets

| Treatment in lbs/A | Number of Applications | Sugar at Harvest-% | Sugar Content After 124 Days Storage-% | Weight Loss After Storage- lbs/ton/day | Sugar Loss After Storage- loss/ton/day | Extractable Sugar Loss- lbs/ton/day |
|---|---|---|---|---|---|---|
| 0 Ethylene | 0 | 17.19 | 14.44 | 0.113 | 0.458 | 0.451 |
| 1.4 | 1 | 16.31 | 14.72 | 0.082 | 0.268 | 0.346 |
| 1.4 | 3 | 16.92 | 14.86 | 0.187 | 0.359 | 0.378 |
| 2.8 | 1 | 17.02 | 14.94 | 0.110 | 0.318 | 0.327 |
| 2.8 | 3 | 16.91 | 14.77 | 0.110 | 0.359 | 0.383 |
| | | | Mean of all ethylene versus control | | | |
| | | | Control | | 0.458 | 0.451 |
| | | | All Ethylene | | 0.326 | 0.359 |
| | | | Percent Difference | | −28.8 | −20.4 |

Table III shows the effect of soil injected ethylene on invert sugars in harvest sugar beets. Invert sugar (glucose and fructose) forms during storage from degradation of sucrose. Soil injected ethylene inhibits the formation of invert sugar during storage. Invert sugar was determined by the tetrazonium method of A. Carruthers and A. E. Wooton (1955 Int. Sug. J. 57:193).

TABLE III

Effect of Soil Injected Ethylene on Invert Sugars in Harvested Sugar Beets

| Treatment in lbs/A | Number of Applications | Time of Sample | Invert Sugars g/100 RDS | Increase In Invert Sugars g/100 RDS | Mean of All Ethylene Versus Control g/100 RDS | Percent Difference |
|---|---|---|---|---|---|---|
| 0 | 0 | in | 0.644 | | | |
| | | out | 1.785 | 1.141 | 1.141 | |

TABLE III-continued
Effect of Soil Injected Ethylene on Invert Sugars in Harvested Sugar Beets

| | | | | | | |
|---|---|---|---|---|---|---|
| 1.4 | 1 | in | 0.602 | | | |
| | | out | 0.962 | 0.360 | | |
| 1.4 | 3 | in | 0.650 | | | |
| | | out | 0.786 | 0.136 | 0.510 | −55.2 |
| 2.8 | 1 | in | 0.541 | | | |
| | | out | 1.121 | 0.580 | | |
| 2.8 | 3 | in | 0.491 | | | |
| | | out | 1.453 | 0.962 | | | in = Invert sugars determined at harvest
out = Invert sugars determined after 124 days storage Invert Sugar Formation Plus Respiration Loss

| | Sugar Loss, lbs/ton/day | Percent Difference |
|---|---|---|
| Control | 0.431 | |
| Ethylene (all treatments) | 0.347 | −19.5 |

Table IV shows the ethylene evolution from stored sugar beets treated with ground injected ethylene. The table shows that beets treated with ground injected ethylene display a lower ethylene evolution from the beet tissue which indicates a much lower respiration during storage than the untreated control.

TABLE IV
Stored Sugar Beet Ethylene Evolution From Field Soil Injected Ethylene

| Treatment | Number of Applications | Replication I Ethylene Evolved in parts/billion | Replication II Ethylene Evolved in parts/billion |
|---|---|---|---|
| Control | 0 | 90 | 75 |
| 1.4 lbs/acre | 1 | 40 | 50 |
| 1.4 lbs/acre | 3 | 50 | 40 |
| 2.8 lbs/acre | 1 | 50 | 40 |
| 2.8 lbs/acre | 3 | 40 | 35 |

Respiration of sucrose to carbon dioxide and water accounts for a major portion of the sucrose lost during storage. Sucrose is also lost in the stored beet when it is hydrolized to invert sugars. Under normal storage conditions respiration and invert sugar formation account for 85% to 95% of the total sucrose degradation. Invert sugars indirectly increase the storage loss by decreasing extraction of sucrose in the factory process. The loss of sucrose during storage amounts to a monetary loss to the industry of millions of dollars each year.

What is claimed is:

1. A method for reduction of sucrose loss during storage of sugar beets due to respiration and invert sugar formation which comprises injecting ethylene gas into the soil between and near the middle of rows of growing sugar beets at spaced intervals in amounts sufficient to reduce respiration and inhibit invert sugar formation in the harvested beets, at a depth of from 6 to 8 inches beneath the soil when the beets have reached the fifth leaf stage.

2. The method of claim 1 when the ethylene is injected at about six foot intervals in the amounts of from about 1.4 to 2.8 pounds per acre in from one to three applications.

* * * * *